(12) United States Patent
Riedel et al.

(10) Patent No.: US 11,404,152 B2
(45) Date of Patent: Aug. 2, 2022

(54) MEDICAMENT DOSAGE DATA COLLECTION

(71) Applicant: SANOFI-AVENTIS DEUTSCHLAND GMBH, Frankfurt am Main (DE)

(72) Inventors: Stephan Riedel, Frankfurt am Main (DE); Isabel Klein, Frankfurt am Main (DE); Alexander Allerdings, Frankfurt am Main (DE); Christian Nessel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 113 days.

(21) Appl. No.: 15/522,436

(22) PCT Filed: Nov. 10, 2015

(86) PCT No.: PCT/EP2015/076169
§ 371 (c)(1),
(2) Date: Apr. 27, 2017

(87) PCT Pub. No.: WO2016/075122
PCT Pub. Date: May 19, 2016

(65) Prior Publication Data
US 2017/0316178 A1    Nov. 2, 2017

(30) Foreign Application Priority Data
Nov. 11, 2014  (EP) .................... 14192728

(51) Int. Cl.
*G16H 20/13* (2018.01)
*G16H 20/17* (2018.01)
*G16H 30/20* (2018.01)

(52) U.S. Cl.
CPC ............ *G16H 20/13* (2018.01); *G16H 20/17* (2018.01); *G16H 30/20* (2018.01)

(58) Field of Classification Search
CPC ............. G06F 19/3468; G06F 19/3462; G06F 19/325; G16H 20/13; G16H 20/17; G16H 30/20
See application file for complete search history.

(56) References Cited

U.S. PATENT DOCUMENTS 6,277,099 B1    8/2001   Strowe et al.
6,658,396 B1   12/2003   Tang et al.
(Continued)

FOREIGN PATENT DOCUMENTS

CN   102427840    4/2012
CN   103153371    6/2013
(Continued)

OTHER PUBLICATIONS

International Search Report and Written Opinion in International Application No. PCT/EP2015/076169, dated Mar. 11, 2016, 10 pages.
(Continued)

*Primary Examiner* — Jason B Dunham
*Assistant Examiner* — Steven G. S. Sanghera
(74) *Attorney, Agent, or Firm* — Fish & Richardson P.C.

(57) ABSTRACT

A data collection device is configured to capture images of a dosage indicator of a medicament delivery device and, if an injection is administered without prior confirmation of a dosage amount, to prompt the user to set a value for the delivered medicament dosage amount for storing in a dosage log. For example, the determination may be based on specific confirmation from the user or detecting a zero dosage amount in captured images. A suggested dosage amount may be displayed to the user, for example a highest or more recently programmed dosage amount prior to the injection or based on one or more previously confirmed dosage amounts. The data collection device may use one or
(Continued)

more of optical character recognition, optical pattern recognition and determination of direction of rotation of a dosage adjustment component to determine whether an injection is being, or has been, administered and/or a suggested dosage amount.

13 Claims, 11 Drawing Sheets

(56) References Cited

U.S. PATENT DOCUMENTS

| | | | |
|---|---|---|---|
| 8,708,957 B2 * | 4/2014 | Jespersen | A61M 5/31525 604/135 |
| 2006/0167419 A1 | 7/2006 | Fiechter et al. | |
| 2013/0245545 A1 | 9/2013 | Arnold et al. | |

FOREIGN PATENT DOCUMENTS

| | | | |
|---|---|---|---|
| CN | 103153372 | 6/2013 | |
| JP | 2001-087386 | 4/2001 | |
| JP | 2006-187630 | 7/2006 | |
| JP | 2008-514249 | 5/2008 | |
| JP | 2010-042277 | 2/2010 | |
| JP | 2015-506770 | 3/2015 | |
| WO | WO 2006/032614 | 3/2006 | |
| WO | WO 2010/124137 | 10/2010 | |
| WO | WO 2010/128493 | 11/2010 | |
| WO | WO-2010128493 A2 * | 11/2010 | ........ A61M 5/31525 |
| WO | WO 2011/117212 | 9/2011 | |
| WO | WO 2012/049142 | 4/2012 | |
| WO | WO 2012/049144 | 4/2012 | |
| WO | WO 2013/120777 | 8/2013 | |
| WO | WO-2013120777 A1 * | 8/2013 | ............. G06F 19/00 |
| WO | WO 2014/023763 | 2/2014 | |
| WO | WO 2014/173772 | 10/2014 | |

OTHER PUBLICATIONS

International Preliminary Report on Patentability in International Application No. PCT/EP2015/076169, dated May 16, 2017, 7 pages.

* cited by examiner

MEDICAMENT DOSAGE DATA COLLECTION

CROSS REFERENCE TO RELATED APPLICATIONS

This application is a U.S. national stage application under 35 USC § 371 of International Application No. PCT/EP2015/076169, filed on Nov. 10, 2015, which claims priority to European Patent Application 14192728.5 filed on Nov. 11, 2014, the entire contents of which are incorporated herein by reference.

TECHNICAL FIELD

The present disclosure relates to an apparatus, system and method for collecting data relating to a medicament dosage from a medication delivery device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dosage window or display of the insulin pen. The dose is then injected by inserting the needle into a suited skin portion and pressing an injection button of the insulin pen.

To be able to monitor insulin injection, for instance to prevent false handling of the insulin pen, to keep track of the doses already applied or to provide a basis for decisions regarding changes and/or continuation of medical treatment, it is desirable to measure information related to a condition and/or use of the injection device, for example, one or more of the injected insulin type, dose and timing of the injection, in a manner that is reliable and accurate.

WO2011/117212 A1 and WO2013/120777 A1 disclose apparatuses configured for releasable attachment to a medical device or for releasably receiving at least a part of the medical device, such as an injection pen. The apparatus comprises one or more optical sensors for determining information relating to a condition or use of the medical device, such as a dosage to be dispensed by the device, programmed into the device by a user. In particular, the apparatus disclosed in WO2013/120777 A1 is configured to, if a user does not press a confirmation button prior to performing an injection, to confirm the dosage amount detected by the one or more optical sensors, a graphic may be displayed suggesting that the user confirms the displayed dose.

For applications such as monitoring medicament dosages, it is important that the sensor data is obtained and processed reliably. In particular, it is important that the recorded dosage, and any indications provided to the user regarding a currently programmed dosage, are accurate, to avoid administration of an incorrect dosage amount.

SUMMARY

According to a first aspect, a data collection device includes a camera, a display, a user interface configured to receive confirmation of a medicament dosage amount programmed into a medicament delivery device, and a processing arrangement configured to capture images of a medicament dose indicator of the medicament delivery device using the camera, display at least a part of the images on a display of the data collection device, determine whether an injection has been administered without prior user confirmation of the medicament dosage amount programmed into the medicament delivery device based on one or more of the images and, in response to a determination an injection has been administered without the prior user confirmation, prompt the user to set a medicament dosage amount for the administered injection for storing in a dosage log, receive a user input of setting the medicament dosage amount and store the medicament dosage amount.

This aspect also provides a medicament delivery system including such a data collection device and a medicament delivery device. In some embodiments, the data collection device is configured for attachment to the medicament delivery device. Such attachment may be releasable, so that the data collection device can be reused with different medicament delivery devices. The medicament delivery device may be an injector pen, such as an insulin injector pen.

Such a data collection device may improve the reliability of recording the delivery of medication to a user, by detecting the occurrence of an injection with an unknown dosage and requesting that the user rectifies the omission promptly.

For example, a dosage log may be maintained in which collected data pertaining to injections administered by the user may be stored. Such data may include one or more of medicament dosage amounts, medicament types and the data and time of the administration of an injection. Such a dosage log may be stored in the data collection device. Alternatively, or additionally, the data collection device may transmit the data to another device where the log is maintained. Such logs may be used to monitor and/or review the user's treatment, for example, when deciding whether changes should be made to the user's medication.

Further, the dosage amounts presented on the display are taken from captured images, without performing a procedure such as optical character recognition to identify the optical dosage amount shown in the image. By using the image, rather than an identified numerical value, the risk of administrating an incorrect dosage due to an erroneous numeral value being identified automatically and displayed may be reduced.

The determination that an injection has been administered without prior confirmation of the medicament dosage amount may be based on input received from the user, such as a specific confirmation that an injection has been performed or an instruction to begin setting of the medicament dosage amount of an administered injection. Alternatively, or additionally, the administration of an injection may be performed automatically, for example, by detecting changes in the dosage amount displayed by the medicament dosage indicator and/or by determining when the displayed dosage amount is a predetermined number, such as zero. Particularly where automatic detection is used, the user may be asked to confirm whether the injection has been administered, to distinguish between a situation in which an injection has been administered without confirmation of the medicament dosage amount and another situation where an injection has not been administered. This may take the form of a specific request for user to provide confirmation, however the receipt of a user instruction to begin setting of a medicament dosage amount may also be treated as confirmation that an injection has been performed.

Prompting the user may include one or more of requesting that the user confirms a suggested dosage amount, requesting that a user provides input indicating the dosage amount, for example by adjusting the suggested dosage amount, and requesting the user indicates whether an unspecified dosage amount is to be recorded.

Setting a dosage amount by a user may include user input confirming a suggested dosage amount displayed by the data collection device and/or user input adjusting a displayed dosage amount. Alternatively, the user may provide specific input indicating an unknown or unspecified medicament dosage amount.

The processing arrangement may be configured to determine that an injection has been administered based on a determination of a medicament dosage amount shown in one or more images of the medicament dosage indicator captured by the camera. For example, the processing arrangement may determine whether a dosage amount shown by the medicament dosage indicator in an image captured by the camera is equal to zero and to determine that the injection has been administered based at least in part on detection of a zero dosage amount or other predetermined dosage amount.

The user interface may be configured to allow a user to indicate the programmed medicament dosage amount by indicating a numerical value in response to the prompt. For example, the processing arrangement may be configured to display an image of a suggested dosage amount to the user and to prompt the user by requesting confirmation of the suggested dosage amount. The processing arrangement may also allow the user to adjust the suggested dosage amount or to proceed with recording the injection with an unknown dosage amount. Where a suggested dosage amount is displayed, the suggested dosage amount may be a highest dosage amount programmed into the delivery device prior to the injection identified from a captured image, or a most recent dosage amount programmed into the delivery device prior to the injection shown in a part of a captured image, of an amount based on one or more confirmed medicament dosage amounts of respective injections administered previously, such as a most recently confirmed dosage amount or an average of multiple previously confirmed dosage amounts. The display of the suggested dosage amount may be in the form of a graphic showing a numerical value, or part of one of the images captured by the camera showing a medicament dosage amount. The data collection device may allow a user to select one from the image showing the suggested dosage amount and a plurality of stored reference images to indicate the medicament dosage amount delivered in the injection. In another example, the user may be requested to re-program the medicament delivery device with the previously administered dosage amount so that the camera can capture a new image for user confirmation.

To determine whether an injection has been administered, the processing arrangement may be configured to determine one or more of the numerical value of a medicament dosage amount displayed by the medicament dosage indicator, whether the medicament dosage amount displayed by the medicament dosage indicator is increasing or decreasing and/or whether the medicament dosage indicator in one of the captured images shows a dosage amount of zero.

According to another aspect, there is provided a method of collecting medicament dosage information from a medical delivery device using a data collection device, the method including capturing images of a medicament dose indicator of the medicament delivery device using a camera of the data collection device, displaying the images on a display of the data collection device, the data collection device determining whether an injection has been administered by the medicament delivery device without prior user confirmation of the medicament dosage amount programmed into the medicament delivery device based on one or more of the images, and the data collection device, in response to a determination an injection has been administered without the prior user confirmation, prompting the user to indicate the medicament dosage amount programmed into the medicament delivery device for the injection.

The determination that an injection has been administered may be based on a determination of a medicament dosage amount shown in one or more images of the medicament dosage indicator captured by the camera using at least one of optical pattern recognition and optical character recognition. For example, the determination may be based at least in part on a determination of whether a dosage amount shown by the medicament dosage indicator in an image captured by the camera is equal to a predetermined amount, such as zero.

The determining that the injection has been administered may be based on a determination of whether the dosage amount shown by the medicament dosage indicator is decreasing.

The prompting of the user may include displaying a suggested dosage amount and permitting at least one of user confirmation and adjustment of the suggested dosage amount.

BRIEF DESCRIPTION

Example embodiments will now be described with reference to the accompanying figures, of which:

DETAILED DESCRIPTION OF THE DRAWINGS

In the following, embodiments will be described with reference to collecting data from an insulin injection device, such as Sanofi's SoloSTAR® pen. The present disclosure is however not limited to such application and may equally well be deployed with injection devices that eject other medicaments, or other types of medicament delivery devices.

Figure 1:
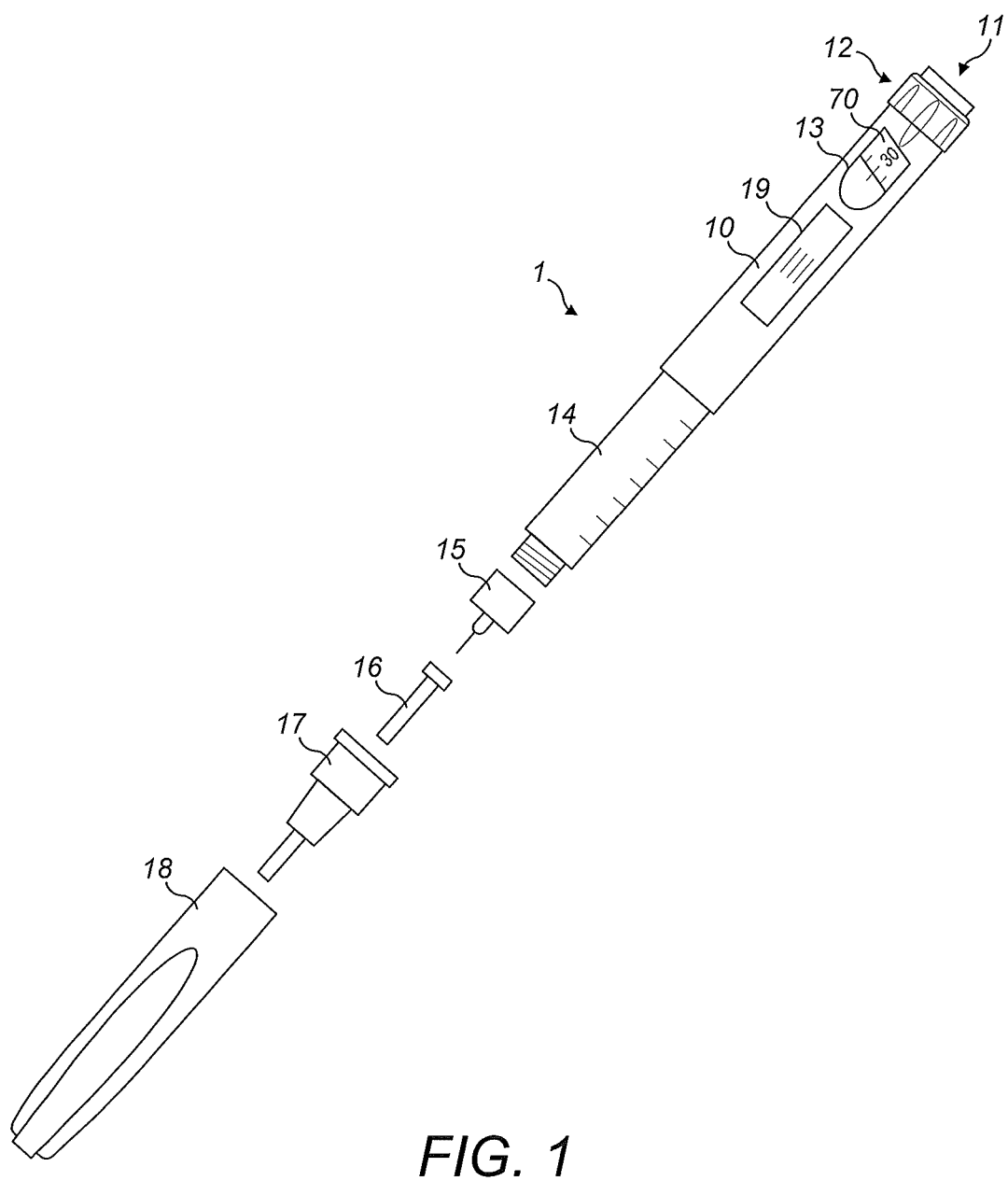
FIG. 1 is a block diagram of a device according to a medical delivery device.

FIG. 1 is an exploded view of an injection device 1 which, in this particular example, represents Sanofi's SoloSTAR® insulin injection pen. In this example, the injection device 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently from the display shown in FIG. 1.

The dosage window 13 may be in the form of an aperture in the housing 10, which permits a user to view a limited portion of a number sleeve 70 that is configured to move when the dosage knob 12 is turned. In order to facilitate taking images of the numbers displayed in the dosage window 13, the number sleeve 70 may have a matte surface.

A label 19 may be provided on the housing 10. The label 19 includes information about the medicament included within the injection device, including information identifying the medicament. The information identifying the medicament may be in the form of text. The information identifying the medicament may also be in the form of a color.

For example, the label 19 may have a background, or include a shaded element such as a border having a color that corresponds to a particular type of medicament that is provided in the injection device. Alternatively, or additionally, the label may include a code, such as a barcode or QR code, or a RFID tag or similar device that stores such information. Alternatively, or additionally, more parts of the injection device, such as an injection button 11 or the dosage knob 12, may be formed of a material having a color that corresponds to the medicament. Optionally, a part of an insulin container (not shown) within the injection device 1 may include a color-coded portion that indicates a medicament type and may be viewable through the dosage window 13. The information identifying the medicament may be in the form of a black and white pattern, a color pattern or shading.

Turning the dosage knob 12 causes a mechanical click sound to provide acoustic feedback to a user. The numbered sleeve 70 mechanically interacts with a piston in insulin container 14. When needle 15 is stuck into a skin portion of a patient, and the injection button 11 is pushed, the insulin dose displayed in the dosage window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting 2 IU of insulin and pressing injection button 11 while holding injection device 1 with the needle 15 upwards. For simplicity of presentation, in the following, it will be exemplarily assumed that the ejected doses substantially correspond to the injected doses, so that, for instance when making a proposal for a dose to be injected next, this dose equals the dose that has to be ejected by the injection device. Nevertheless, differences (e.g. losses) between the ejected doses and the injected doses may of course be taken into account, particularly with regard to a "prime shot".

Figure 2:
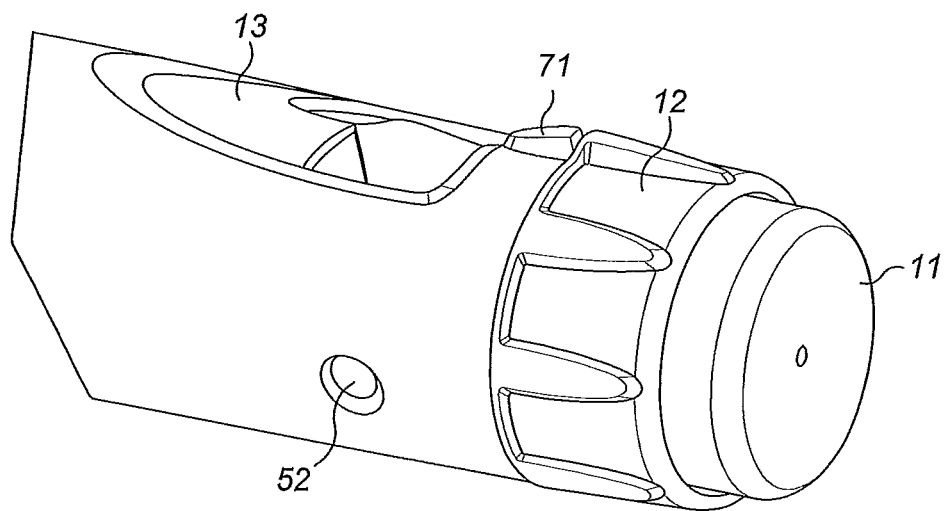
FIG. 2 is a perspective view of a part of the device of FIG. 1.

FIG. 2 is a close-up of one end of the injection device 1. In the particular example shown in FIG. 1, a locating rib 71 is located between the viewing window 13 and the dosage knob 12.

FIGS. 3 to 6 depict apparatuses that may be used to collect data, such as insulin type, dosage amount and timing of injection, from the injection device of FIG. 1.

Figure 3:
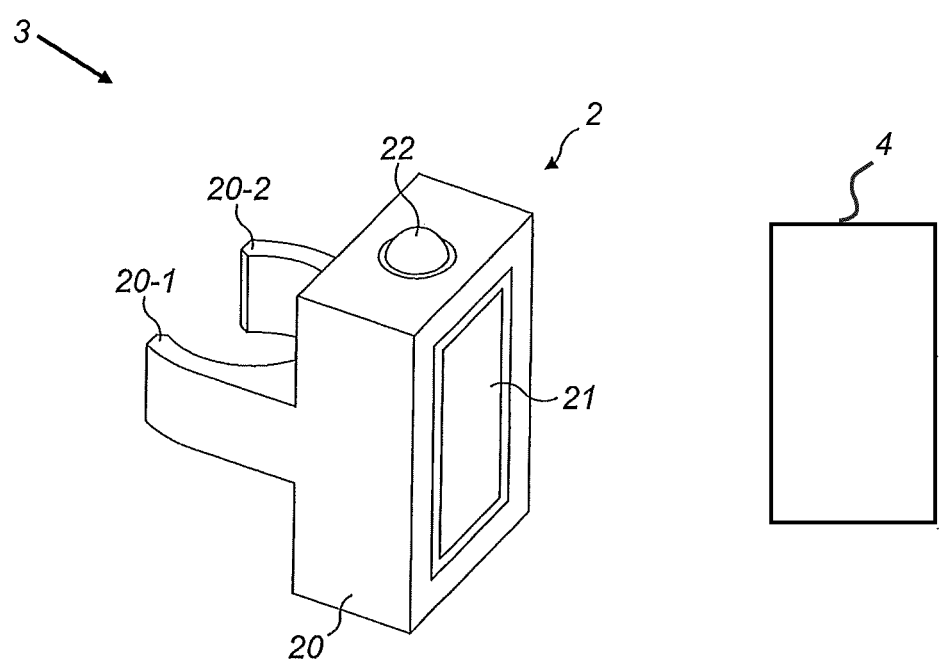
FIG. 3 is a perspective view of a system including a data collection device according to an embodiment, which may be used with the medical delivery device of FIG. 1.

FIG. 3 depicts a data collection system 2, including a data collection device 3. The data collection device 3 is configured to be attached to the injection device 1. In this particular embodiment, the data collection device 3 includes clips 20-1, 20-2, which are configured to embrace the housing 10 to releasably attach the apparatus 2 to the injection pen 1. Alternatively, the clips 20-1 and 20-2 may for instance be replaced by a ring-shaped member (not shown), into which the upper portion of housing 10 of injection device 10 may be inserted.

The housing 20 of the data collection device 3 may include formations to align the data collection device 3 with the dosage window 13 and prevent rotation there between. Such formations may include as a recess (not shown) on the housing 20 of the data collection device 3, configured to receive the locating rib 71 or other formations (not shown) on the housing 10, and/or protrusions (not shown) on inner surfaces of the arms 20-1, 20-2, configured to engage recesses 52 on the housing 10 of the injection device 1.

The data collection device 3 includes a display 21, and a power button 22 for switching the data collection device 3 on and off and/or activating functions such as transmitting data to another device 4. In this particular example, the data collection device 3 is configured to capture images of at least part of the dosage window 13, and to transmit the images and other data to and, optionally, receive data from, the other device 4 via a network such as a cellular telecommunications network, Wi-Fi network, Bluetooth® network or similar. The other device 4 may be a mobile telephone, tablet computer, server or other computing device.

Figure 4:
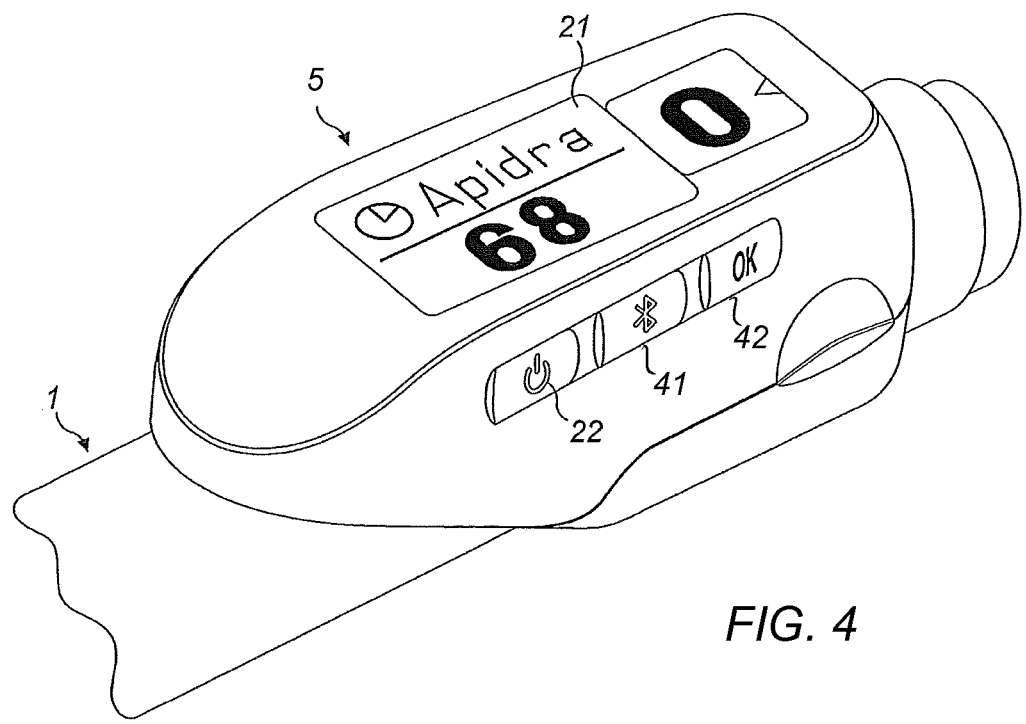
FIG. 4 depicts a data collection device according to another embodiment, attached to the medical delivery device of FIG. 1.

FIG. 4 depicts a data collection device 5 according to another embodiment when attached to the injection device 1. In this example, the data collection device 5 has a housing formed of two housing sections 40-1, 40-2 connected by a hinge (not shown), that may be clipped around the housing 10 of the injector pen 1, engaging the locating rib 71 and recesses 52 as described above in relation to the data collection device 3 of FIG. 3. In this particular example, additional buttons 41, 42 are provided to allow a user to control communications from the data collection device 5 to the other device 4 using communication button 41 and to confirm information or commands displayed on the display 21 using command button 42.

Figure 5:
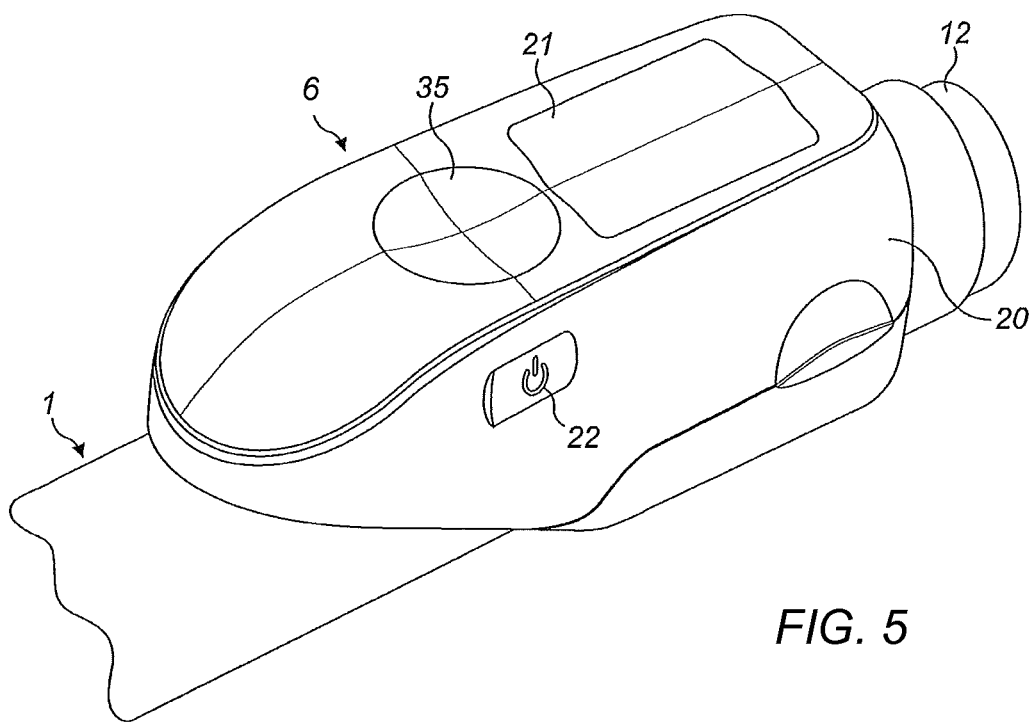
FIG. 5 depicts a data collection device according to another embodiment, attached to the medical delivery device of FIG. 1.

FIG. 5 depicts a data collection device 6 according to yet another embodiment when attached to the injection device 1. The data collection device 6 of FIG. 5 differs from the data collection device 5 of FIG. 4 in that a multifunction button 35 is provided instead of the communication button 41 and command button 42 shown in FIG. 4.

Figure 6:
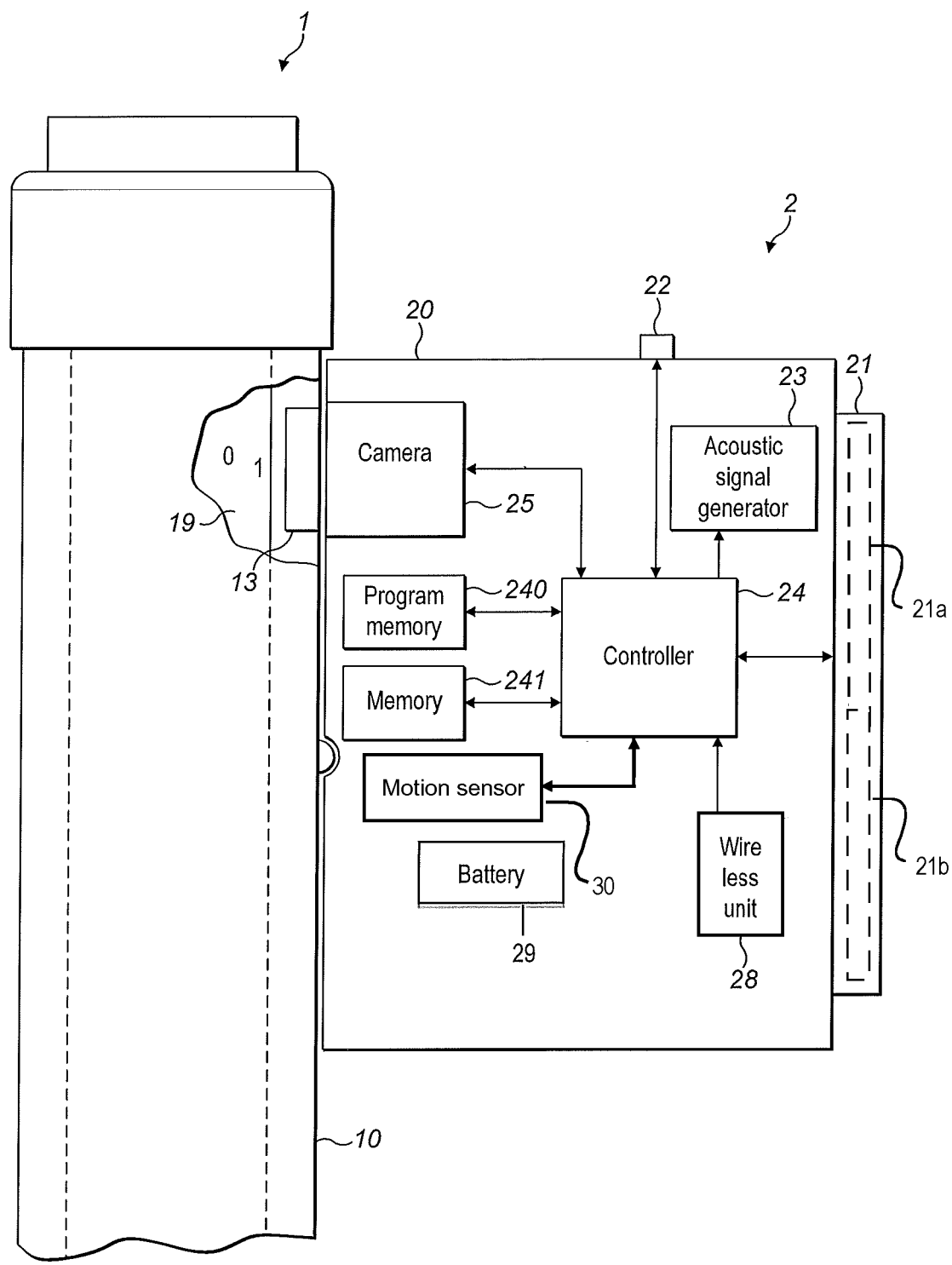
FIG. 6 is a block diagram of the data collection device shown in FIG. 3.

FIG. 6 is a block diagram of the data collection device 3, but may be equally applicable to the data collection devices 5, 6 shown in FIGS. 4 and 5. The data collection device 3 is an electronic device, including a controller 24. The controller 24 is a processing arrangement including one or more processors, such as a microprocessor, a Digital Signal Processor (DSP), Application Specific Integrated Circuit (ASIC), Field Programmable Gate Array (FPGA) or the like.

The data collection device 3 is equipped with built-in camera 25 that, when the data collection device 3 is attached to the injection pen 1, is arranged to capture the images of at least part of the dosage window 13. Since the data collection device 3 obscures the dosage window 13 from the user's view, part, or all, of the images captured by the camera 25 may be presented to a user on the display 21, to show a medicament dosage amount currently displayed in the dosage window 13.

In this example, the data collection device 3 also includes an acoustical signal generator 23 that, in conjunction with the display 21, may be used for presenting information and/or providing alerts to a user.

In this particular example, the display 21 is configured as a touch screen, to allow a user to input commands or information by touching the display 21 and, optionally, by using a swiping movement across the display 21. For example, the display 21 may include first and second touch-sensitive regions 21a, 21b, to detect swiping movements made by the user in one of two directions, based on the order in which user contact with the first and second touch-sensitive regions 21a, 21b is detected.

The data collection device 3 also includes main memory 241 and program memory 240 configured to store software to be executed by the controller 24, data received from the camera 25 and results of processing such data. Also provided is a wireless unit 28 configured to provide a communication link between the data collection device 3 and the other device 4, and a battery 29, which may be a rechargeable battery.

The data collection device 3 may optionally include further sensors, such as a motion sensor 30, a photometer (not shown) for reading barcode information on the housing 10, one or more acoustic sensors (not shown) for detecting sounds indicative of the programming of a dose into the injection pen 1 and/or administration of an injection.

The controller 24 of the data collection device 3, 5, 6 may be configured to process the images to extract information relating to the medicament dosage amount shown in the images captured by the camera 25, and to send the extracted information to the other device instead of, or as well as, the images captured by the camera 25. For example, the controller 24 may be configured to perform one or more of optical pattern recognition and optical character recognition (OCR) on one or more captured images. Such pattern recognition and/or OCR may be employed for one or more of identifying a displayed medicament dosage amount, determining whether a displayed medicament dosage amount corresponds to a particular value, such as zero IU, to determine a highest dosage amount programmed into the injection device 1 before delivery or a medicament and determining whether a user is programming an increasing or decreasing dosage into the injection device 1.

Figure 7:
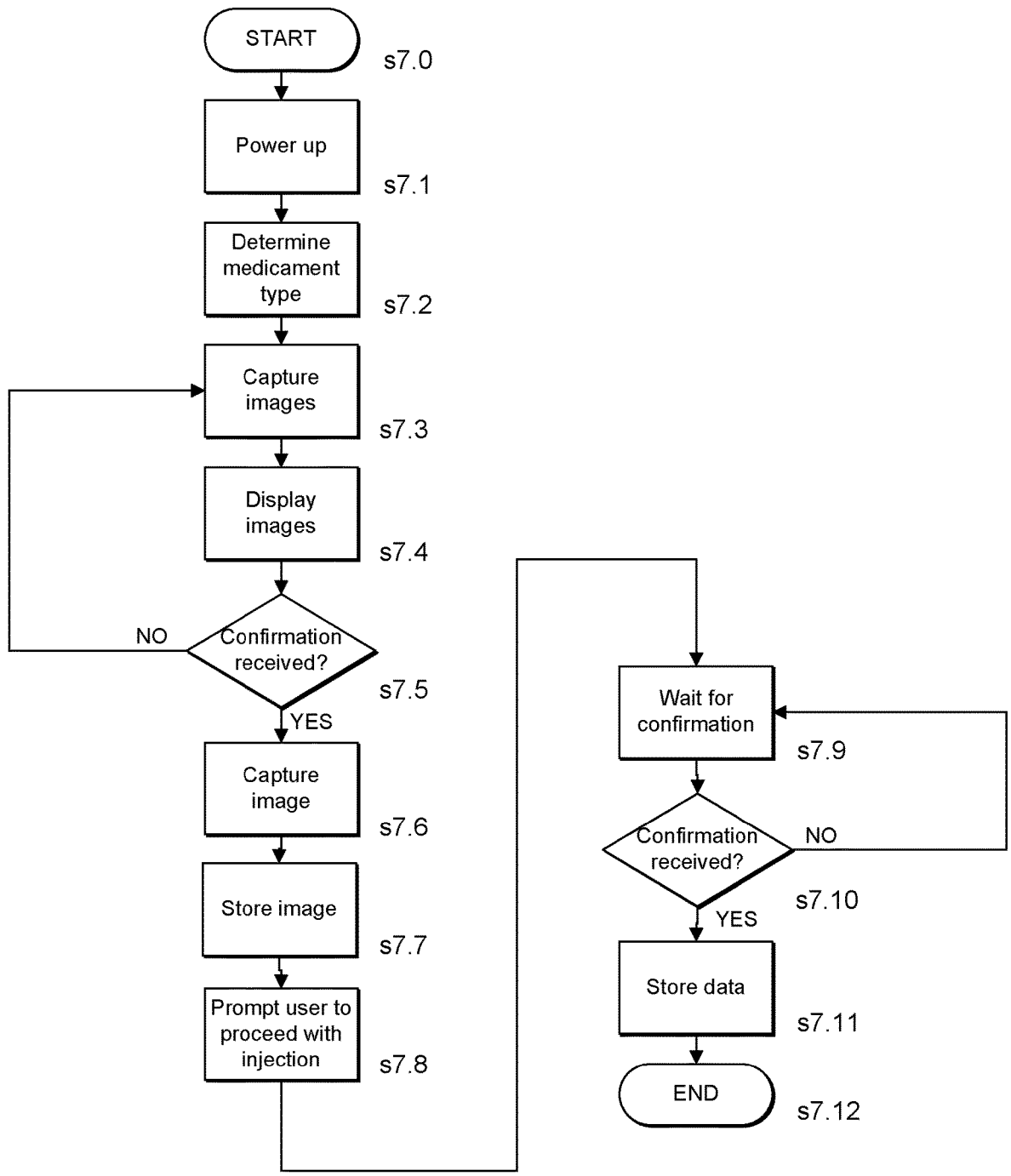
FIG. 7 is a flowchart of a method of determining a medicament dosage using the data collection device shown in FIG. 3, where a user confirms a medicament dosage amount prior to an injection.

FIG. 7 is a flowchart of a method of collecting medicament dosage information using the data collection device 3, in which a user confirms the detected dosage amount before delivery of the medicament.

Starting at step s7.0, the device is powered on (step s7.1), for example, in response to the user pressing the power button 22.

Optionally, the data collection device 3 collects data regarding the type of medicament in the injector pen 1 (step s7.2). For example, the camera 25 of the data collection device 3 may capture an image of part of the injection pen that includes a code, or has a color corresponding to, a particular type of medicament, so that the controller 24 may determine the medicament type from a look up table or similar. Other example techniques for identifying the medicament include reading a RFID tag provided on the injector pen or from user input.

The camera 25 then captures images of the dosage window 13 while the user programs the injection pen 1 to deliver a particular medicament dosage amount (step s7.3).

The captured images are displayed on the display 21 (step s7.4), so that the user can view the currently programmed dosage amount while using the dosage knob 12.

The data collection device 3 continues to capture and display images (steps s7.3, s7.4) until it receives an input from the user confirming the medicament dosage amount to be delivered (step s7.5). For example, the user may indicate that the currently displayed dosage amount is the amount to be delivered by pressing one button 22 provided on the data collection device 3 or by touching a particular region 21a, 21b or swiping across the display 21.

In an embodiment where only one button 22 is provided on the housing 10, the controller 24 may be configured to respond to activation of the button 22 by determining whether the button 22 has been pressed for a time period that is shorter, or longer, than a predetermined threshold. For example, if the button 22 is pressed for a time that is shorter than the threshold ("short push"), then the controller 24 may respond by treating the activation of the button 22 as indicating a confirmation ("OK"). On the other hand, if the button 22 is pressed for a time that exceeds the predetermined threshold ("long push"), the controller 24 responds by powering down the data collection device 3.

In embodiments where multiple buttons are provided, for example, in the data collection device 5 of FIG. 4, the user may provide confirmation of a displayed dosage amount by pressing the command button 42.

The controller 24 responds to the user input received at step s7.5 by controlling the camera 25 to capture an image of the dosage window 13 (step s7.6) and then stores the image (step s7.7).

The controller 24 provides an indication to the user to proceed with an injection (step s7.8). For example, the controller 24 may cause the display 21 to show an arrow pointing towards the needle 16, to indicate to the user that the injection button 11 should be pressed along that direction.

The data collection device 3 then waits for confirmation from the user that the injection has been administered (steps s7.9, s7.10). The user may provide confirmation by pressing a button 22, 24, 25 or via the touch screen.

Alternatively, if the data collection device 3 is configured to perform optical character recognition or optical pattern recognition, then the camera 25 may be configured to continue to take images and the decrease of the displayed dosage amount to zero may be detected, suggesting that an injection has been performed, instead of relying on confirmation from the user in steps s7.9 and s7.10.

If the injection has been confirmed (step s7.10), the controller 24 stores information relating to the injection, such as the time of the injection and, optionally, data regarding the medicament type (step s7.11), completing the injection process (step s7.12). Together with the image stored in step s7.7, the stored data provides a record of the injection that may be included in a log of treatment administered by the user, for example, for periodic review by a medical practitioner. The stored data or, if provided, the treatment log may be transmitted to the other device 4 on request by the user.

Figure 8:
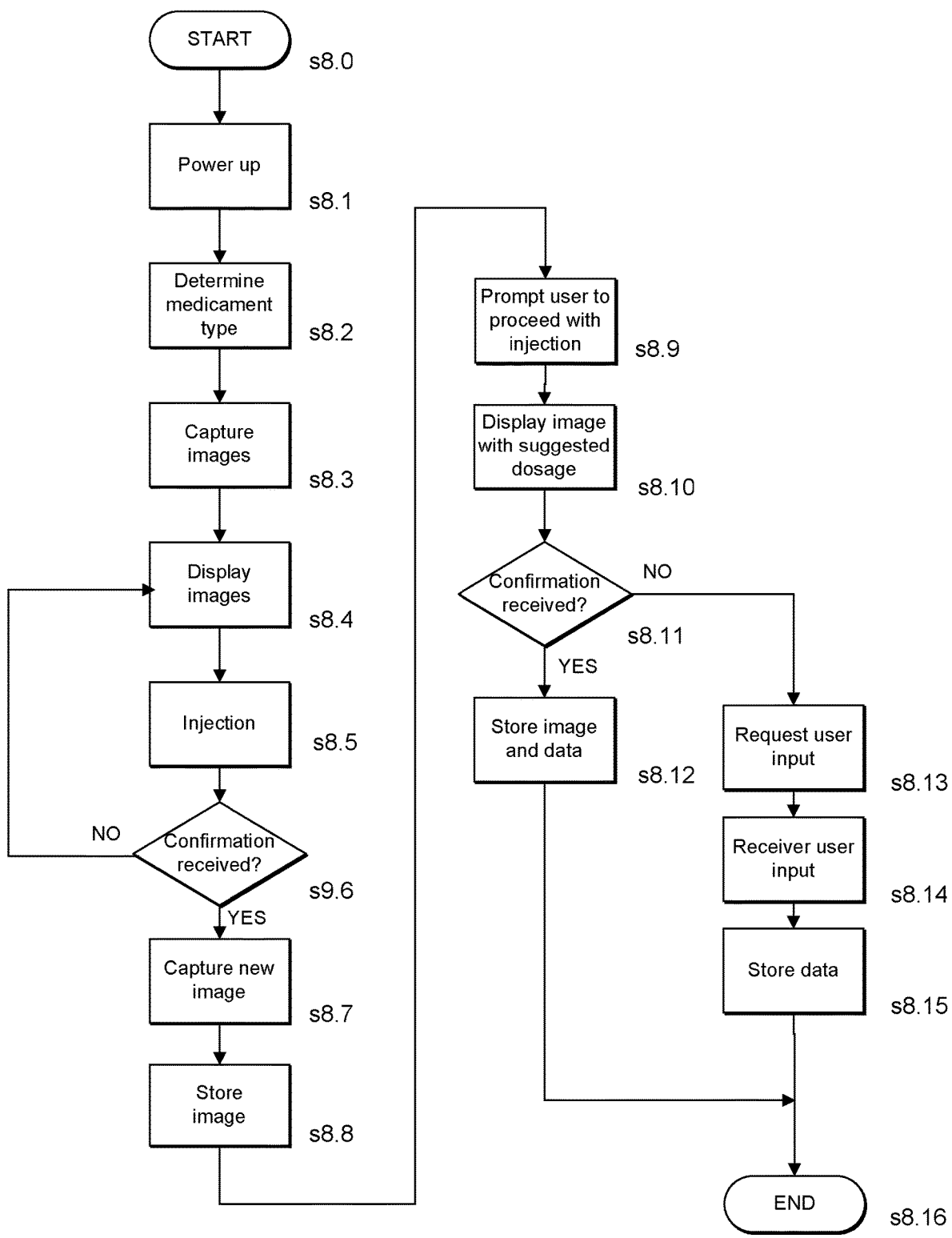
FIG. 8 is a flowchart of a procedure for collecting medicament dosage information after delivery of the medicament, according to an embodiment.

FIG. 8 depicts a procedure according to an embodiment, which may be followed if the user does not confirm the dosage amount before administering the injection. In this particular example, the data collection device 3 need not be configured to perform optical pattern recognition, optical character recognition or determination of changes in the programmed dosage amount.

Steps s8.0 to s8.4 correspond to steps s7.0 to s7.4 of FIG. 7, as discussed above. However, in this example, the user has proceeded to administer the injection (step s8.5) without first confirming the dosage amount. In an injection device 1 such as the SoloSTAR® pen, the dosage amount displayed in the dosage window 13 decreases during an injection stroke, and reaches zero when the programmed dosage amount of medicament has been ejected.

Hence, when the user provides confirmation (step s8.6) by pressing a button 22, 24, 25 or touching the display 21 and a new image is captured and stored (steps s8.7, s8.8), as described above in relation to steps s7.6 and s7.7 of FIG. 7, the newly captured image will show a dosage amount of zero.

The data collection device 3 will then prompt the user to proceed with the injection. At this point, the user will become aware of their omission to confirm the programmed dosage amount.

Following a command by the user, for example, by swiping across the display 21, the data collection device 3 will enter a "post-storing" mode, in which the user can indicate the administered dosage amount. The data collection device 3 displays an image showing a suggested dosage amount (step s8.10). For example, the image may be the image showing zero dosage amount captured at step s8.8, or an image captured previously by the camera 25 at step s8.3. Alternatively, a default image showing a predetermined dosage amount, stored previously in the memory units 240, 241, may be displayed.

If the user confirms the suggested dosage (step s8.11), the displayed image is stored (step s8.12), together with other data indicating the time of the injection and, optionally, the medicament type.

If the user does not confirm the suggested dosage (step s8.12), then the user is requested to input a confirmed dosage amount (step s8.13). The confirmed dosage amount is received at step s9.14 and then stored, together with information regarding the time of the injection and, optionally, the medicament type (step s8.15).

Figure 9:
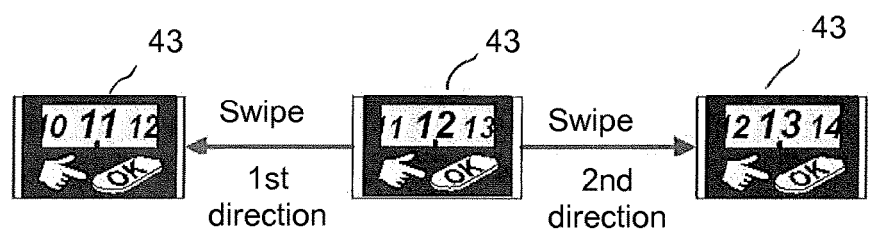
FIG. 9 depicts a display on the data collection device of FIG. 3 when a user inputs a medicament dosage amount via a touch screen.

FIG. 9 depicts an example procedure for user input of the dosage amount using the touch screen, which will be referred to as a "post storing" dialogue. As shown in FIG. 9, a dosage amount is displayed, for example, in a graphic 43 resembling a number sleeve. In this particular example, the user may then increase or decrease the dosage amount indicated on the display by swiping their finger across the display 21, where a swiping motion in a first direction, for example to the left, decreases the indicated dosage amount, and a swiping motion in a second direction, for example to the right, increases the indicated dosage amount. When the correct dosage amount is indicated by the display 21, the user may confirm it by a short push of the button 22 or, where provided, by pressing the command button 42 or touching a predetermined region of the display 21.

Alternatively, the user may turn the dosage knob 12 to reprogram the injection pen 1 with the same dosage amount as the administered injection and then indicate their confirmation of the dosage amount at step s9.13. The controller 24 can then respond to the confirmation by using the camera 25 to capture an image of the programmed dosage amount (not shown) and storing the newly captured image with the other data pertaining to the injection (steps s8.15)

However, if the user simply switches off the data collection device 3 at step s8.11, for example by a long push of the power button 22, the data collection device 3 may simply store data regarding the time of the injection and, optionally, the medicament type, without a specified medicament dosage amount (not shown).

The procedure ends at step s8.16.

Figure 10:
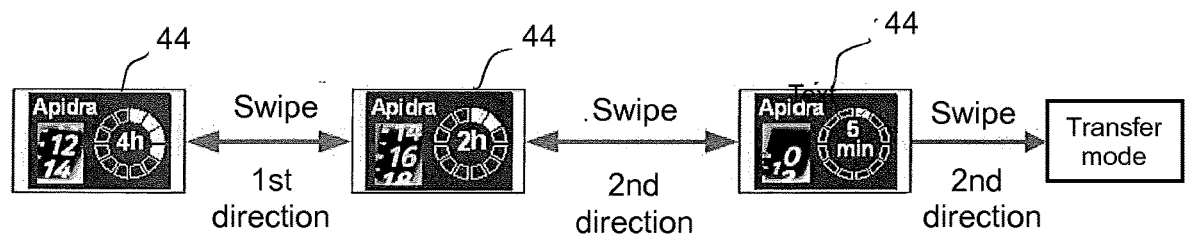
FIG. 10 depicts user navigation through a log of administered injections and a data transfer screen.

FIG. 10 depicts displayed entries 44 in a treatment log, showing how a user might navigate between log entries and a transfer mode. As shown in FIG. 10, a time period since a previous injection is displayed, for example, in a graphic resembling a clock or stopwatch. The user may swipe between successive log entries by swiping across the display 21 in first and second directions. A swiping motion in the second direction, starting from a most recent entry, may switch the data collection device 3 into a transfer mode, in which the user can command the data collection device 3 to transfer the stored data to the other device 4 via the wireless unit 28.

In the procedures shown in FIGS. 7 and 8, the data collection device 3 is not used to extract medicament dosage information from a captured image, and determination of the medicament dosage amount is performed by the other device 4. However, in other embodiments, the controller 24 of the data collection device 3 may be configured to process the captured image to determine the displayed dosage amount. Examples of such other embodiments will now be described, with reference to FIGS. 11, 12 and 13.

Figure 11:
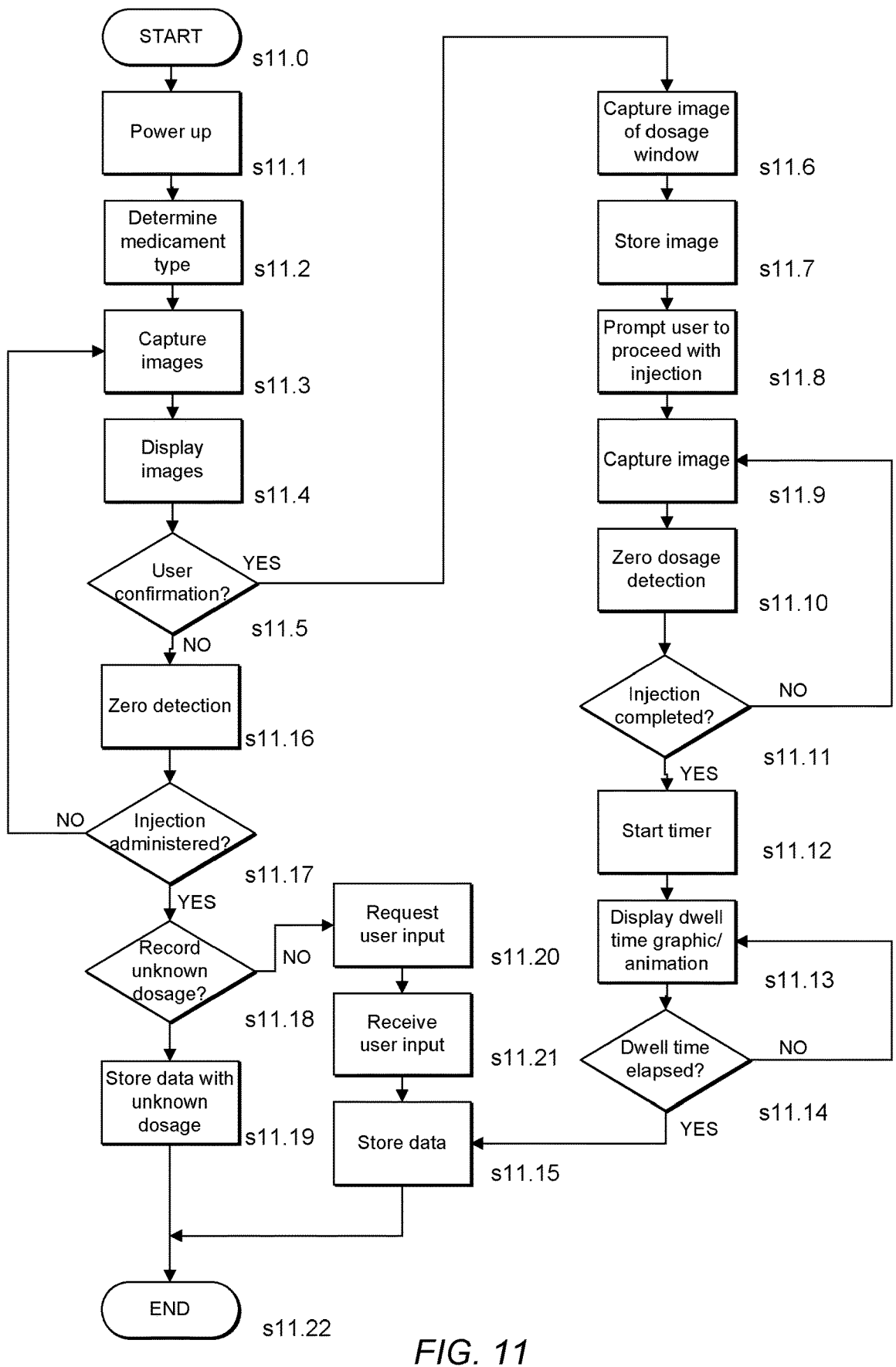
FIG. 11 is a flowchart of a method of collecting medicament dosage data according to another embodiment.

FIG. 11 is a flowchart of another method of collecting medicament dosage information using a data collection device 3 which, in this case, is configured to perform optical pattern recognition. In this procedure, the user is not required to confirm completion of an injection.

Starting at step s11.0, the device is powered on (step s11.1), for example, in response to the user pressing the power button 22.

The data collection device 3 then determines the type of medicament and present medicament information, such as the name of the medicament, on the display 21 (step s11.2), as described above in relation to step s7.2 of FIG. 7.

The camera 25 then captures images of the dosage window 13 while the user programs the injection pen 1 to deliver a particular medicament dosage amount (step s11.3). The captured images are displayed on the display 21 (step s11.4), so that the user can view the currently programmed dosage amount.

If the user confirms the programmed dosage amount (step s11.5), then the controller 24 responds by controlling the camera 25 to capture an image of the dosage window 13 (step s11.6) and stores the captured image in one of the memory units 240, 241 (step s11.7).

The controller 24 provides an indication to the user to proceed with an injection (step s11.8). For example, the controller 24 may cause the display 21 to show an arrow pointing towards the needle 16, to indicate to the user that the injection button 11 should be pressed.

The camera 25 continues to capture images of the dosage window 13 during the injection stroke (step s11.9). As the injection is administered, the number shown in the dosage window 13 decreases. As noted above, in an injection device 1 such as the SoloSTAR® pen, when an injection stroke is completed, the dosage window 13 displays a dosage amount of "0". The controller 24 performs optical pattern recognition on the images captured by the camera 25 to identify when the value of "0" is shown (step s11.10) and determine that administration of the injection has been completed (step s11.11).

The optical pattern recognition, or optical pattern correlation, performed by the controller 24 at step s11.10 may be less computationally intensive than a full OCR technique, since it is not necessary to identify individual numerical characters in the captured images. For example, the controller 24 may be configured to scan a reference image of the dosage window 13, stored in one of the memory units 240, 241, in which a dosage amount of "0" is displayed, and determine whether the correlation between the captured image and the reference image exceeds a predetermined threshold.

The steps of image capture and pattern recognition (steps 11.9, 11.10, 11.11) are repeated until it is determined that the dosage amount displayed in the dosage window 13 is zero (step s11.11). This zero detection triggers a timer (s11.12), which indicates a "dwell time" during which the user is instructed to keep the needle in the injection site to allow the medicament to disperse. During the dwell time, the data collection device 3 may present a graphic or animation on the display 21 (step s11.13) to indicate to the user the need to wait before removing the needle from the injection site. For example, the display 21 may present an animation showing an hourglass.

Once the dwell time has elapsed (step s11.14), the controller 24 stores data relating to the delivery of the medicament (step s11.15).

If, on the other hand, user confirmation of the dosage amount is not received at step s11.5, then the controller 24 performs optical pattern recognition on the most recently captured image, to determine whether the dosage amount shown is "0" (step s11.16). If the dosage amount is determined to be zero, then it is determined that an injection has been administered without the user confirming the programmed dosage amount (step s11.17).

Figure 12:
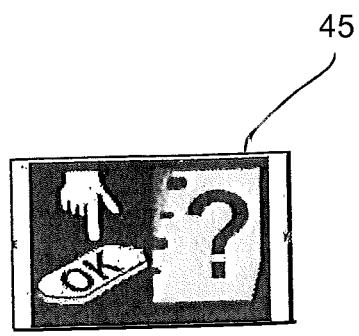
FIG. 12 depicts a display on a data collection device during part of the method of FIG. 11.

If it is determined, at step s11.17, that an injection has been administered without prior confirmation of the dosage amount, then the data collection device 3 prompts the user to indicate whether the injection is to be recorded with an unknown dosage amount. For example, a graphic 46 showing an image of a dosage amount with a question mark, "?", instead of a number, may be presented on the display 21, as shown in FIG. 12. For example, a user may decide to record an unknown dosage amount if the injection was not performed, and the detection of a zero dosage was instead caused by a user resetting the dosage amount to zero.

If an indication that the injection is to be recorded with an unknown dosage is received from the user (step s11.18), then the available data for the injection, such as the time and, optionally, the medicament type, are stored with an indication that the dosage amount is unknown (step s11.19).

If, instead, the user indicates that the injection is to be recorded with a specified dosage amount, then the data collection device 3 enters the "post-storing" mode, to request user input set a dosage amount, for example, using the dialogue discussed above with reference to FIG. 9 (step s11.20).

When user input setting a medicament dosage amount is received (step s11.21), data including the confirmed dosage amount, time of injection and, optionally, medicament type, is stored (step s11.15).

The procedure then ends (step s11.22).

Figure 13:
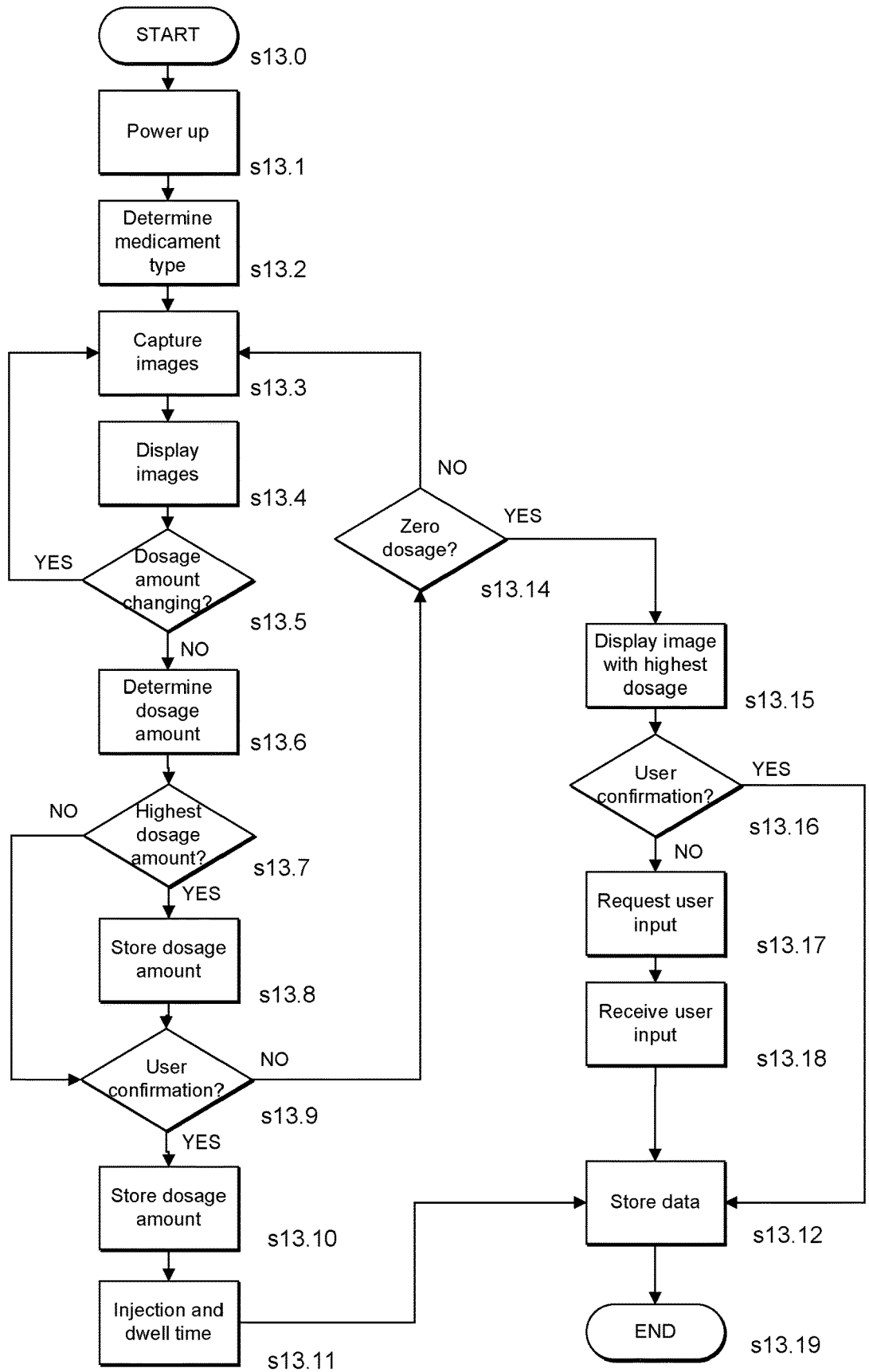
FIG. 13 is a flowchart of a method according to yet another embodiment.

FIG. 13 depicts a method according to another embodiment, for use with a data collection device 3 that is capable of performing optical character recognition (OCR).

Starting at step s13.0, the data collection device 3 is powered on (step s13.1). The data collection device 3 then determines the type of medicament and present medicament information, such as the name of the medicament, on the display 21 (step s13.2), as described above in relation to step s8.2 of FIG. 8.

The camera 25 captures images of the dosage window 13 while the user programs the injection pen 1 to deliver a particular medicament dosage amount (step s13.3). The captured images are displayed on the display 21 (step s13.4), so that the user can view the currently programmed dosage amount.

If it is determined that the dosage amount displayed in the dosage window 13 is changing (step s13.5), suggesting that the programming of the medicament dosage amount is still in progress, then another image is captured by the camera (step s13.3) and displayed (step s13.4) and those steps are repeated until it is determined that the dosage amount is not changing (step s13.5). The dosage amount may be considered to not be changing, if it is determined that the dosage amount has not changed for a predetermined period of time. The predetermined period of time may be in the range of 0.1 to 1 second. In particular, the predetermined period of time may be in the range of 0.1 to 0.4 seconds, for example a period of 0.2 seconds.

The determination of whether the dosage amount may be based on the detection of movement of the dosage knob 12 or number sleeve 70 by the motion sensor 30, where provided. In other embodiments, for example in a data collection device without a motion sensor 30, the controller 24 may determine that the dosage amount displayed in the dosage window 13 has not changed for the predetermined period of time (step s13.5) based on the images captured by the camera 25. For instance, if the images of the numbers on the number sleeve 70 appear blurred, it may be determined that the user is still operating the dosage knob 12 and the programming of the dosage amount is not yet complete. If, however, the image of the numbers in the dosage window 13 is sharp, or if consecutive images captured during the predetermined period of time match each other, it may be determined that the dosage amount is no longer changing and the programming of the injection device 1 might have been completed (step s13.5).

If it is determined that the dosage amount displayed in the dosage window 13 has not changed for a predetermined period of time (step s13.5), suggesting that the user might have completed programming of the medicament dosage amount, then the image is processed by the controller 24 and the displayed dosage amount is determined using OCR (step s13.6).

In another embodiment, the dosage amount may be determined (step s13.6) without first checking for changes in the dosage amount (step s13.5). However, by limiting the determination of the dosage amount using OCR (step s13.6) to when the dosage is not changing (step s13.5) may help to conserve computing and power resources in the data collection device 3 which, in turn, may extend the time intervals between charging or replacing the battery 29.

Optionally, the controller 24 may perform pre-processing of the captured image as a precursor to the OCR, to assess and, if required, improve image quality by executing the following steps:
Defective and bad pixel correction
Light correction
Distortion
Jitter For example, an exposure control algorithm may adjust the operation of the camera 25 to correct for images that are too bright or too dark by controlling exposure parameters for the camera 25.

The optional pre-processing may also include adjusting the image by correcting skew of the characters displayed in the dosage window 13 based on the orientation of the injection device 1 relative to the camera and/or any slanting of the characters displayed in the dosage window 13. For instance, the numbers in the dosage window 13 might be slanted for ease of recognition and positioning by a user, but may be easier to decode by the data collection device 20 if the slant is removed.

The controller 24 then attempts to recognize characters from the image of the dosage window 13 using an OCR algorithm stored in the memory units 240, 241, in order to determine a number or other dosage indication displayed in the dosage window 13.

The OCR process comprises the steps of:
Binarization
Segmentation
Pattern matching
Position calculation There may, in some embodiments, be two OCR algorithms that are operated in parallel to enhance reliability. The two OCR algorithms have the same input (image) and are intended to provide the same output. They both perform similar steps however the individual methods used in each step may vary. These two OCR algorithms may differ in one of the binarization, segmentation, pattern matching and position calculation steps or in more than one of these steps. Having two OCR-parts which use different methods to provide the same result increases the reliability of the entire algorithm as the data has been processed in two independent ways.

In the OCR process, the color or greyscale image obtained from the camera 25 and adjusted as described above is converted into a purely black and white image through a binarization process. In an example where dark numbers are presented on a bright background in the dosage window, the black and white image would indicate the presence of digits with black pixels and the absence of digits with white pixels. In some embodiments a fixed threshold is used to separate between black and white pixels. Pixels that have a value at or above the threshold become white, pixels below the threshold become black in the binarized picture. A high threshold will lead to artefacts (black parts in white areas), whereas a low threshold has the risk that in some cases parts of digits are missing. In some embodiments, the threshold is chosen so that in no case are parts of digits are missing because the algorithm is in general robust against artefacts (i.e. an accurate OCR process can be performed in the presence of some artefacts). In tests where an image was analyzed using 256 grey values, a threshold value of 127 showed good results.

The use of a fixed threshold is possible where light correction has been performed, for example, in the pre-processing. The combination of the light correction and the fixed threshold is similar to a windowed mean binarization. A windowed mean binarization compares the pixel-value with the mean value of the pixels of the area where it is located. Performing the light correction step before the distortion and slant correction steps means that more information is available to be used for the OCR process, which has been shown to yield better results on the edges and corners of the picture. Alternatively, the Otsu threshold method may be applied to the captured greyscale image to produce a binary image. In some alternative embodiments, the binarization may be omitted and the OCR part of the algorithm may be performed on the captured color or greyscale image.

Segmentation is then performed. The goal of this part of the algorithm is to determine the exact location of each visible or partly visible number in the image. To achieve this, the algorithm defines the boundaries of the visible digits by finding the edges of the digits. This is generally accomplished in two steps, which may be performed in any order. The controller 24 may perform a "vertical projection" in which the pixel columns making up the binarized image are analyzed. Each pixel column is analyzed individually and the sum of the number of black pixels in each column is computed. In some embodiments, only a pixel column having zero black pixels defines the edge of a number. Alternatively, a low threshold for the number of black pixels may be set to account for dirt, scratches and other disturbances. Difference values for adjacent columns are calculated and the boundary having the greatest difference represents the edge of the number. Additionally, the pixel content of overlapping groups of columns (e.g. three adjacent columns) may be calculated to aid in determining the horizontal edges of the numbers.

The controller 24 then performs a "horizontal projection" in which the pixel rows making up the binarized image are analyzed. This proceeds in a similar manner to that as described above with regard to the vertical projection.

The expected result of the horizontal projection is added to that of the vertical projection such that the edges of the visible numbers are identified. The controller may be pre-programmed with the expected height (in pixel rows) of a full number, and so is able to recognize the presence of partially visible numbers.

In another embodiment, the "horizontal projection" and the "vertical projection" may be based on an analysis where the sum of white pixels is computed, provided that the expected number of white pixels in each row and column is known.

Knowing the exact location allows for using only the part of the image which represents the visible number or numbers for the next steps in the OCR process. By this any impact of other objects besides the number, e.g. dirt, scratches and other disturbances, can be reduced. Further, the total number of pixels to be processed in subsequent steps, e.g. in the pattern matching step, is also reduced. This helps reduce resource requirements. This also helps increase performance. In addition, knowing the exact location also supports determining the vertical position relative to the center of the image.

The next step in the OCR process is to select one of the visible numbers to be decoded and identified. This is done by designating one of the numbers as the "primary digit row". The primary digit row is selected based on which visible number has the greatest height. This is because all of the numbers printed on the sleeve 70 have approximately the same height and it can be assumed that the number having the greatest height will be fully visible and therefore easy to decode with a high degree of certainty. The primary digit row is the number which is subsequently used to determine the dose dialed into the injection device 1.

A standard injection device 1 for self-administration of insulin can inject any number of units of medicament from 1 to 80 IU. Therefore, in order to properly decode the number identified as the primary digit row, it must be determined whether the number consists of one or two digits. The controller 24 therefore performs a series of steps in order to determine whether each number consists of one or two digits, and in the latter case, to separate the digits from each other. The controller 24 may use the column pixel information previously calculated for this purpose.

After this, the controller 24 determines whether the selected primary digit row is wider than a pre-defined "maximum digit width" value. The controller 24 may be pre-programmed with information relating to the expected size of the numbers in the captured images, so that a maximum expected width for a single digit can be defined. In order to increase reliability, the maximum width may be set as a small number of pixel columns more than the widest number. If the width of the primary digit row is the maximum digit width or less, it is assumed that the row contains a single digit. If the primary digit row is too wide to be a single digit, then a second vertical projection is then performed on the primary digit row (rather than on the whole image). In addition, the expected width of each individual digit may be used to predict the point at which the separation should occur.

In some injection devices 1, the numbers may be displayed quite close together in the dosage window, owing to limited available space and the need for the numbers to be readable to a user. Thus, after binarization, the two digits making up the number may not be cleanly separated, i.e. there may not be a column having no black pixels between the two digits. In this case, the expected width of each individual digit is again used to predict the point at which the separation should occur. If the predicted column contains black pixels, then the deviations of this column from adjacent columns are calculated to determine the best separation point. In this situation, as it is not clear whether the black pixels in the chosen separating column belong to the left or right digit, they are ignored. This has been shown to have a minimal effect on the reliability of the OCR process to correctly identify the digits.

A pattern matching process is then performed to identify the digits in the primary digit row. Templates for each number may be pre-programmed via the app and the identified digits may then be compared to these templates. In a straight forward approach, the pattern matching could be performed on a pixel-by-pixel basis. However, this may require high computing power and may be prone to position variation between the image and the template. Where templates are used, the controller 24 may perform other types of manipulation on the images numbers, for example by changing the size of one or more digits, cropping the numbers to a defined pixel area and shearing numbers printed in an italic font into an upright position. These manipulations may be performed before a pattern matching comparison with the stored templates. Alternatively, these manipulations may be performed in preprocessing before the binarization process. Additional shading, distortion and exposure correction may also be performed.

In some other embodiments, a feature recognition process is performed. Features may be horizontal, vertical or diagonal lines, curves, circles or closed loops etc. Such features may be recognized in the image of the selected number and compared with templates.

In yet further embodiments, the pattern matching algorithm may be based on a vector comparison process. For example, the templates may be in the form of vectors describing the position and length of each line (continuous run) of black pixels. In one example, the position and length relate to the absolute position in the respective line. In another example, the position and length relate to a vertical line extending through the center of the template. The captured binary image of each digit may similarly be converted into vectors and compared with each stored template in turn to find the best match. When comparing the vectors of the captured image with a particular digit template, any deviations result in a penalty being applied for the likelihood of a match between the image and that template. The magnitude of the penalty may depend on the number of missing or extra black pixels in the image compared to the template. After the digit image has been compared with each template and all of the penalties have been applied a decision is made as to which digit is present. In good optical conditions, the correct template will have a very low penalty, while all other templates will have a high penalty. If the primary digit row consists of two digits, this process is performed on both digits and the controller 24 can then combine the outcomes to produce a final result for the number.

Special measures may exist for certain digits. For example, "1" deviates substantially in width from all other digits resulting in common misdetections. To counter this, if a binary image of a digit is wider than the expected width of "1", then it receives an additional detection penalty when being compared with the stored vector template of "1".

In some exceptional cases, if the confidence level in the result of the pattern matching of the primary digit row is below a certain threshold (e.g. 99%), then the processor may perform a second pattern matching process on one or more of the other visible or partially visible numbers. Since the order of the numbers is known, this second pattern matching can act as a check that the first pattern matching returned the correct result.

If the confidence level in the result is still not high enough, then a new image may be captured using the camera 25 and processed by the controller 24.

If the digit or digits of the primary digit row have been successfully identified, a weighting function is applied in order to determine a dose displayed in the dosage window 13. To formulate the weighting function, the vertical position of the primary digit row relative to the center of the dosage window 13 may be determined. This may be done by calculating the offset of the middle pixel row comprising the primary digit row relative to a pixel row representing a center line of the dosage window 13 in the image.

For example, in some embodiments the camera 25 comprises a rectangular 64×48 array of photosensitive elements. The resulting binary image is a pixel array having these same dimensions. The $24^{th}$ and/or $25^{th}$ pixel row may be designated as the central row of the image. The position of the middle pixel row comprising the primary digit row is determined. The offset, in pixel rows, between the middle pixel row comprising the primary digit row and the central row or rows of the image is then calculated. This offset may be positive or negative depending on the direction of the offset. The offset is converted into a fraction by dividing it by the distance (in pixel rows) between successive numbers before being applied to the determined numbers accordingly. The offset therefore allows for determining the rotational position of the number relative to the sensor. If the central pixel row of the primary digit row is the same as the central pixel row of the image, then the offset is zero and the position is equal to the primary digit row number. However, there is likely to be some offset in most circumstances.

The distance between successive numbers printed on the number sleeve 70 is constant, since the numbers represent a dose which is related to a discrete mechanical movement of the injection device mechanism. Therefore, the distance (in pixel rows) between successive numbers in the captured image should also be constant. The expected height of the numbers and spaces between the numbers may be pre-programmed into the app. As an example, the expected height of each numbers may be 22 pixels and the expected height of the spaces between the numbers may be 6 pixels. Therefore, the distance between the central pixel rows of successive numbers would be 28 pixels.

Continuing this example, if the pixel rows are numbered sequentially from the top to the bottom of the image, the application of the weighting function may be defined mathematically as:

Position=primary digit row number+[2×offset/(expected height of number+expected height of space)]

Where offset=image row number corresponding to the center of the dosage window−primary digit row central row number Thus, if the primary digit row is in the upper half of the image, then the offset is positive and if the primary digit row is in the lower half of the image, then the offset is negative. For example, if the number shown in the primary digit row is "6" and the offset is zero, then the calculated position would be:

Position=6+[2×0/(28)]=6

Thus a result of "6" would be returned as expected.

In another example, where 75 IU are dialed into the injection device 1, if the top number, "74", is selected as the primary digit row and there is a positive offset of 11 pixel rows according to the equation above, and again assuming a combined number/space height of 28 pixels, the calculated position would be:

Position=74+[2×11/(28)]=74.79

This result is then rounded up to the nearest whole number, to give a position determination of "75" as expected.

The skilled person will appreciate that the above described weighting function and position determination represents only one example and that numerous other calculation methods may be used to arrive at the same result. The skilled person would also appreciate that the above described mathematical calculation may be modified and improved to reduce the computation time. Thus the exact form of the weighting function is not essential to a definition.

In some injection devices, due to space restrictions and the need for the numbers to be of a certain size, only even numbers are presented in the dosage window 13. In some other injection devices, only odd numbers may be displayed. However, any number of units of medicament can be dialed into the injection device 1. In other injection devices, both even and odd numbers may be presented and it may be possible to dial half-unit doses into the injection device. The injection device may be limited to a maximum dialed dose of 80 IU. Alternatively, only every $3^{rd}$, $4^{th}$ or $5^{th}$ number may be displayed and doses between the numbers may be indicated by tick marks. In view of this, the OCR algorithm may cause the controller 24 to identify the numbering sequence used in the injection device 1. For example, the user may be prompted to enter information regarding the injection device 1 into the data collection device 3 or the information may be obtained from the image, for example from the text or a barcode on the label 19 may be used. The controller 24 may consult a look-up table or other information indicating the numbering sequences used for various injection devices 1 stored in the memory units 240, 241. The controller 24 may then determine the selected dose based on both OCR data and the appropriate numbering sequence for the injection device 1. Alternatively, or additionally, a modified form of the weighting function may be used, as the height of the numbers and size of the space between the numbers may also be modified.

The method may optionally include post-processing, such as performing sanity checks and hysteresis calculations. Alternatively, the result of the OCR process may be finalized without post-processing.

If the image is the first image on which the controller 24 has performed OCR since the data collection device 3 was powered on at step 14.1, or the controller determines whether the result of the OCR process indicates a dosage amount that is higher than the dosage amounts extracted from any previously processed images (step s13.7), the result of the OCR process is stored in the memory units 240, 241 as a currently displayed dosage amount (step s13.8).

If the user confirms the dosage amount (step s13.9), then the dosage amount is stored in the memory units 240, 241 as a confirmed dosage amount (step s13.10). After administration of the injection and elapse of the dwell time (step s13.11), as described above in relation to FIG. 11, information including the time of the injection and, optionally, the medicament type, is stored (step s13.12).

However, the user may proceed to administer the injection without first confirming the dosage amount. In this case, the camera 25 continues to capture images of the dosage window 13 (step s13.6) but it will be indicated that the dosage amount is changing (step s13.5).

When the dosage amount displayed in the dosage window 13 reaches zero, then no further changes will be detected (step s13.3) and the controller 24 will determine the dosage amount (step s13.6). However, the determined dosage amount of zero will not be the highest dosage amount (step s13.7). Since the user has not confirmed the dosage amount (step s13.8), the controller 24 checks whether the dosage amount determined at step s13.6 is zero (step s13.14). If not, then steps s13.3 to s13.14 are repeated until either the user confirms the programmed dosage amount (step s13.9) or a dosage of zero is detected (step s13.14).

Figure 14:
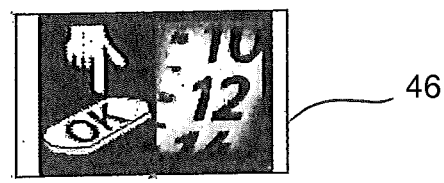
FIG. 14 depicts a display on a data collection device during part of the method of FIG. 13.

If a zero dosage amount is detected at step s13.14, then it is determined that an injection has been administered with an unconfirmed dosage amount. The controller 24 then prompts the user for further input to determine how to proceed. In this particular example, a graphic 46 showing a suggested dosage amount may be presented on the display 21 (step s13.15), as shown in FIG. 14, for the user to confirm or reject (step s13.16). Here, the suggested dosage amount is the highest dosage amount stored previously at step s13.8.

If the user confirms the suggested dosage amount (step s13.16), then the image showing the highest dosage amount, now confirmed by the user, the time of the injection and, optionally, the medicament type, is stored (step s13.12).

If the user does not confirm the suggested dosage amount (step s13.16), then the data collection device 3 enters the post-storing mode. The data collection device 3 presents a request to the user to input the administered dosage amount on the display 21 (step s13.17), for example using the swiping motions as shown in FIG. 10, and receives the input (step s13.18). In some embodiments, the initial graphic 43 displayed in the post-storing mode may correspond to a default dosage amount, a previously confirmed dosage amount or an average, such as mean, median or mode, of a plurality of previously confirmed dosage amounts.

Alternatively, the user may turn the dosage knob 12 to reprogram the injection pen 1 with the same dosage amount as the administered injection and then indicate their confirmation of the dosage amount. The controller 24 can then respond to the confirmation by using the camera 25 to capture an image of the programmed dosage amount to be stored as an indication of the confirmed dosage amount.

After the user input has been received (step s13.18), information indicating the confirmed dosage amount, the time of the injection and, optionally, the medicament type, is stored (step s13.12).

The procedure then ends (step s13.19).

Figure 15:
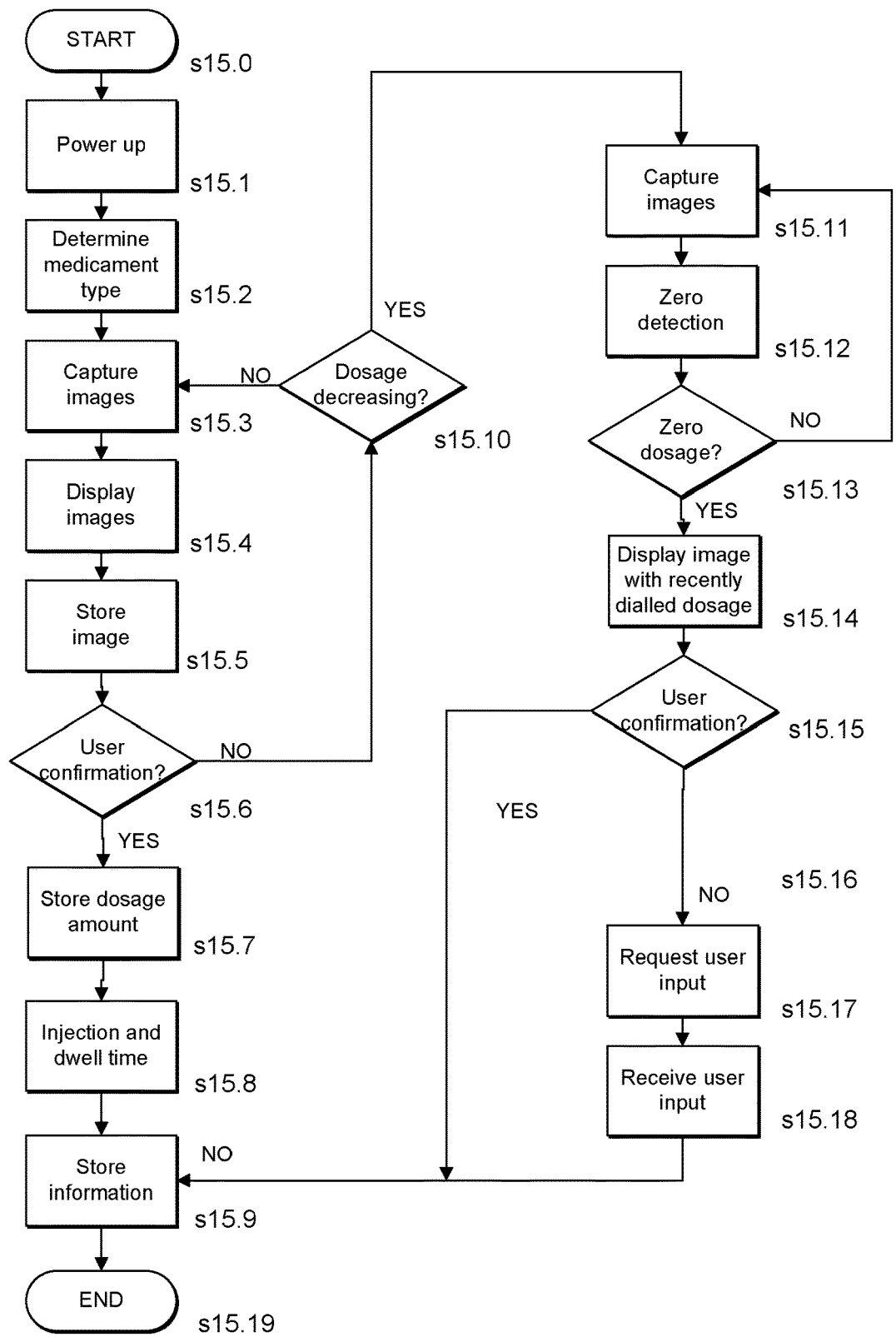
FIG. 15 is a flowchart of a method according to a further embodiment.

FIG. 15 depicts a method according a further embodiment, for use with a data collection device 3 that is capable of detecting whether the dosage amount shown in the dosage window 13 is decreasing, for example, by detecting a direction of rotation (DDR) of the dosage knob 12 as the displayed dosage amount changes.

Starting at step s15.0, the data collection device 3 is powered on (step s15.1). The data collection device 3 then determines the type of medicament and present medicament information, such as the name of the medicament, on the display 21 (step s15.2), as described above in relation to step s8.2 of FIG. 8.

The camera 25 captures images of the dosage window 13 while the user programs the injection pen 1 to deliver a particular medicament dosage amount (step s15.3). The captured images are displayed on the display 21 (step s15.4), so that the user can view the currently programmed dosage amount and then stored in one of the memory units 240, 241 (step s15.5).

If the user then confirms the dosage amount (step s15.6), then the data collection device 3 stores the confirmed dosage amount (step s15.7) and prompts the user to begin the injection. After the completion of the injection stroke and the elapse of the dwell time (step s15.8), information including the confirmed dosage amount, time of the injection and, optionally, the medicament type is transmitted to the other device 4 (step s15.9) for storage and/or onward transmission (step s15.10).

If the user does not confirm the dosage amount (step s15.6), the controller 24 then determines whether the dosage amount displayed in the dosage window 13 is decreasing (step s15.11). This determination may be based on the images captured by the camera 25. In other embodiments, the data collection device 3 detect the direction of movement using a sensor, for example, based on the passage of reflective tick marks on the number sleeve as the dosage knob 12 is turned, as detected by the photometer, or by the motion sensor 30.

In the present example, where the injection device 1 is a SoloSTAR® pen, the displayed dosage amount returns to zero during the administration of an injection, the displayed dosage amount would start from zero when programming the injection device 1. Hence, the displayed dosage amount in the dosage window 13 would initially increase. While an injection is administered, the displayed dosage amount would gradually decrease.

If it is determined that the dosage amount shown in the dosage window 13 is not decreasing (step s15.10), then another image is captured (step s15.3), displayed (step s15.4) and stored (step s15.5), since programming of the medicament dosage amount might still be in progress.

If it is determined that the dosage amount shown in the dosage window 13 is decreasing (step s15.10), suggesting that an injection may be in the process of being administered, then the camera 25 continues to capture images of the dosage window 13 (step s15.11) and the controller 24 performs optical pattern recognition on those images (step s15.12) to determine whether the displayed dosage amount has fallen to zero (step s15.13), suggesting the completion of an injection. The optical pattern recognition and zero detection may be performed in the same manner as that described above in relation to FIG. 14. Alternatively, the data collection device 3 may be configured to determine that an injection has been completed if it is found that the dosage, having been found to be decreasing at step s15.10, is no longer changing for the predetermined period of time at step s15.13.

Steps s15.11 to s15.13 are repeated until it is determined that the dosage window 13 is displaying a dosage amount of zero (step s15.13).

When the dosage amount displayed in the dosage window 13 has returned to zero (step s15.13), the controller 24 displays an image showing a suggested dosage amount for confirmation or rejection by the user (step s15.14). Here, the image is the image most recently captured by the camera 25 at step s15.3 and stored at step s15.5 before the first image indicating a decreasing dosage amount at step s15.10. In other words, the suggested dosage amount is the dosage amount found to be most recently dialed into the injection device 1 by the user. The suggested dosage amount is displayed in a similar manner to that shown in FIG. 14.

The controller 24 then prompts the user for further input to determine how to proceed. If the user responds by confirming the suggested dosage amount (step s15.15), then the image containing the suggested dosage amount, the time of the injection and, optionally, the medicament type, is transmitted to the other device (step s15.9).

Alternatively, if the user does not confirm the suggested dosage amount (step s15.15), then the data collection device 3 enters the post-storing mode. The controller 24 presents a request to the user to input the administered dosage amount on the display 21 (step s15.17), for example using the swiping motions as shown in FIG. 10, and receives the input (step s15.18). The initial graphic 43 displayed in the post-storing mode may be based on one or more previously confirmed dosage amounts, as discussed above in relation to FIG. 13.

The controller 24 then stores information including the confirmed dosage amount, the time of the injection and, optionally, the medicament type (step s15.9).

The process then ends (step s15.19).

The above embodiments are examples only, and it is noted that alternative data collection devices, having different combinations of data processing capabilities and/or sensors may be provided. As noted above, certain functions, such as the storing of a dosage log, or one or more of OCR, ZD and DDR, may be performed by the other device 4 as well as, or instead of, the data collection device 3, 5, 6.

While the embodiments above have been described in relation to collecting data from an insulin injector pen, it is noted that embodiments may be used for other purposes, such as monitoring of injections of other medicaments or other medical processes. Embodiments may also be used to for non-medical purposes, for example, in monitoring the operation of other types of equipment for safety reasons.

The invention claimed is:

1. A data collection device comprising:
a camera;
a user interface configured to receive confirmation of a medicament dosage amount programmed into a medicament delivery device; and
a processing arrangement comprising one or more processors and configured to:
cause the camera to capture a first plurality of images of a medicament dose indicator of the medicament delivery device;
cause to display at least a part of the first plurality of images on a display of the data collection device;
determine, based on a subset of images in the first plurality of images, that a medicament dosage amount indicated by the medicament dose indicator is decreasing;
in response to determining that the medicament dosage amount is decreasing:
cause the camera to capture a second plurality of images of the medicament dose indicator of the medicament delivery device,
perform optical pattern correlation on the second plurality of images, and
identify when a value of "0" is shown in one or more of the second plurality of images;
determine whether an injection has been administered without a prior user confirmation of the medicament dosage amount programmed into the medicament delivery device based on whether the value of "0" is identified as being shown in the one or more of the second plurality of images; and
in response to an identification that the value of "0" is shown in one or more of the second plurality of images by performing optical pattern correlation on the one or more of the second plurality of images, and a determination that the injection has been administered without the prior user confirmation:
cause to display, on the display of the data collection device, an image by the camera including one or more images of numerical values, wherein the displayed image corresponds to the most recent image, in the first plurality of images, that was captured prior to capturing the earliest image in the subset of images;
cause to prompt the user to set the medicament dosage amount for the administered injection for storing in a dosage log by requesting the user to select one of the one or more images,
receive a user input for setting the medicament dosage amount, and
store the medicament dosage amount.

2. The data collection device according to claim 1, wherein the processing arrangement is configured to determine that the injection has been administered based on a determination of the medicament dosage amount shown in one or more of the plurality of first images.

3. The data collection device according to claim 2, wherein the processing arrangement is configured to determine that the injection has been administered based on determining that the dosage amount shown by the medicament dose indicator is decreasing.

4. The data collection device according to claim 2, wherein the processing arrangement is configured to determine whether the dosage amount shown by the medicament dose indicator in an image in the plurality of first images is equal to zero, and to determine that the injection has been administered based, at least in part, on the zero dosage amount.

5. The data collection device according to claim 1, wherein the processing arrangement is configured to determine a highest dosage amount programmed into the medicament delivery device prior to the injection, and to display the highest dosage amount to the user, wherein the processing arrangement is configured to prompt the user by requesting confirmation of the highest dosage amount.

6. The data collection device according to claim 1, wherein the processing arrangement is configured to determine a suggested medicament dosage amount based on one or more confirmed medicament dosage amounts of respective injections administered previously, and to display the suggested medicament dosage amount to the user, wherein the processing arrangement is configured to prompt the user by requesting confirmation of the suggested medicament dosage amount.

7. The data collection device according to claim 1, wherein the processing arrangement is configured to determine a medicament dosage amount shown in a most recent one of the plurality of first images captured by the camera prior to the injection, and to display the determined dosage amount to the user, wherein the processing arrangement is configured to prompt the user by requesting a confirmation of the determined dosage amount.

8. The data collection device according to claim 1, wherein:
the processing arrangement is configured to determine whether the medicament dosage amount displayed by the medicament dose indicator is increasing or decreasing;
the processing arrangement is configured to respond to an indication that the injection is being performed by processing a most recent image captured before a performance of the injection to determine a suggested medicament dosage amount and to display the suggested medicament dosage amount to the user; and the processing arrangement is configured to prompt the user by requesting confirmation of the suggested medicament dosage amount.

9. A medicament delivery system comprising:
a medicament delivery device; and
a data collection device comprising:
a camera;
a user interface configured to receive confirmation of a medicament dosage amount programmed into a medicament delivery device; and
a processing arrangement comprising one or more processors and configured to:
   cause the camera to capture a first plurality of images of a medicament dose indicator of the medicament delivery device;
   cause to display at least a part of the first plurality of images on a display of the data collection device;
   determine, based on a subset of images in the first plurality of images, that a medicament dosage amount indicated by the medicament dose indicator is decreasing;
   in response to determining that the medicament dosage amount is decreasing:
      cause the camera to capture a second plurality of images of the medicament dose indicator of the medicament delivery device,
      perform optical pattern correlation on the second plurality of images, and
      identify when a value of "0" is shown in one or more of the second plurality of images;
   determine whether an injection has been administered without a prior user confirmation of the medicament dosage amount programmed into the medicament delivery device based on whether the value of "0" is identified as being shown in the one or more of the second plurality of images; and
   in response to an identification that the value of "0" is shown in one or more of the second plurality of images by performing optical pattern correlation on the one or more of the second plurality of images, and a determination that the injection has been administered without the prior user confirmation:
      cause to display, on the display of the data collection device, an image by the camera including one or more images of numerical values, wherein the displayed image corresponds to the most recent image, in the first plurality of images, that was captured prior to capturing the earliest image in the subset of images;
      cause to prompt the user to set the medicament dosage amount for the administered injection for storing in a dosage log by requesting the user to select one of the one or more images,
      receive a user input for setting the medicament dosage amount, and
      store the medicament dosage amount.

10. A method of collecting medicament dosage information from a medicament delivery device using a data collection device, the method comprising:
   capturing a first plurality of images of a medicament dose indicator of the medicament delivery device using a camera of the data collection device;
   determining, based on one or more of the first plurality of images, whether an injection has been administered by the medicament delivery device without a prior user confirmation of a medicament dosage amount programmed into the medicament delivery device by, and in response:
      capturing a second plurality of images of the medicament dose indicator of the medicament delivery device using the camera,
      performing optical pattern correlation on the second plurality of images, and
      identifying when a value of "0" is shown in the second plurality of images; and
   in response to an identification that the value of "0" is shown in one or more of the second plurality of images by performing optical pattern correlation on the one or more of the second plurality of images, and the determination that the injection has been administered without the prior user confirmation:
      displaying, on the display of the data collection device, an image by the camera including one or more images of numerical values, wherein the displayed image corresponds to the most recent image, in the first plurality of images, that was captured prior to capturing the earliest image in the subset of images,
      prompting the user to set the medicament dosage amount for the administered injection for storage in a dosage log by requesting the user to select one of the one or more images,
      receiving a user input setting the medicament dosage amount, and
      storing the medicament dosage amount.

11. The method according to claim 10, wherein determining that the injection has been administered is based, at least in part, on a determination of whether the medicament dosage amount shown by the medicament dose indicator in an image in the first plurality of images is equal to a predetermined amount.

12. The method according to claim 10, wherein determining that the injection has been administered is based on a determination of whether the medicament dosage amount in successive ones of the first plurality of images is decreasing.

13. The method according to claim 10, wherein prompting the user comprises displaying a suggested dosage amount and permitting at least one of user confirmation, rejection and adjustment of the suggested dosage amount.

* * * * *